United States Patent
Raman et al.

(10) Patent No.: US 11,071,812 B2
(45) Date of Patent: Jul. 27, 2021

(54) METHODS AND APPARATUS FOR EXTRACTING DOXORUBICIN FROM BLOOD AND MEASURING DOXORUBICIN IN BLOOD

(71) Applicant: Penumbra, Inc., Alameda, CA (US)

(72) Inventors: Karthik Raman, Union City, CA (US); Colin Yee, Fremont, CA (US); Chia-Hung Sze, St. Louis, MO (US); Arthur John Lockhart, San Ramon, CA (US); David Barry, San Ramon, CA (US)

(73) Assignee: PENUMBRA, INC., Alameda, CA (US)

( * ) Notice: Subject to any disclaimer, the term of this patent is extended or adjusted under 35 U.S.C. 154(b) by 258 days.

(21) Appl. No.: 15/608,023

(22) Filed: May 30, 2017

(65) Prior Publication Data

US 2017/0340797 A1     Nov. 30, 2017

Related U.S. Application Data

(60) Provisional application No. 62/343,680, filed on May 31, 2016.

(51) Int. Cl.
*A61M 1/36* (2006.01)
*B01J 39/26* (2006.01)
*B01J 39/04* (2017.01)

(52) U.S. Cl.
CPC ........ *A61M 1/3615* (2014.02); *A61M 1/3679* (2013.01); *B01J 39/04* (2013.01); *B01J 39/26* (2013.01)

(58) Field of Classification Search
CPC ............... A61F 2/013; A61F 2002/015; A61F 2230/0067; A61F 2/01; A61F 2/011; A61M 25/10; A61M 2025/1097; A61M 1/3615; A61M 1/3679; A61M 2025/1052; A61M 25/0029; B01J 39/04; B01J 39/26; B01J 47/08; A61L 31/041; A61L 31/129; A61L 31/145; A61K 2300/00; A61K 31/4365; A61K 31/60; A61K 31/196; A61K 31/404; A61K 31/416; A61K 31/704; A61K 31/7056; A61K 47/26; A61K 47/36; A61K 47/38; A61K 9/0019; A61K 9/19; A61K 9/2018; A61K 9/2027; A61K 9/2054; A61K 9/2059; A61P 43/00; A61P 11/00; A61P 13/08; A61P 13/10; A61P 13/12; A61P 15/00; A61P 19/00; A61P 1/04; A61P 1/16; A61P 1/18; A61P 21/00; A61P 25/00; A61P 25/04; A61P 29/00; A61P 29/02; A61P 35/00; A61P 35/02; A61P 37/02; A61P 37/06; A61P 37/08; A61P 41/00; C08L 1/28; C08L 5/02; C08L 5/08; B01D 2321/16; B01D 61/44; B01D 61/48; B01D 61/52; B01D 65/08; C02F 1/42; C02F 1/4695; C02F 2201/46115; C02F 2201/46185; C08J 2301/28; C08J 2305/02; C08J 2305/08; C08J 3/075; C08J 3/246; G01N 30/8658; G16C 20/10; G16C 20/20; G16C 20/70

See application file for complete search history.

(56) References Cited

U.S. PATENT DOCUMENTS

| | | | | |
|---|---|---|---|---|
| 2010/0041725 | A1* | 2/2010 | Suzuki | A61K 9/2018 514/403 |
| 2012/0283959 | A1* | 11/2012 | Ruzic | G16C 20/70 702/23 |
| 2015/0342975 | A1* | 12/2015 | Geyer | A61K 31/7056 514/34 |

FOREIGN PATENT DOCUMENTS

WO     WO-2014100201 A1     6/2014

OTHER PUBLICATIONS

Dogaroiu et al, Practical implications of GC and HPLC methods for the analysis of drugs of abuse in blood, 2008, p. 97 (Year: 2008).*
Reddy et al, Rapid and sensitive HPLC method for the estimation of doxorubicin in dog blood—The silver nitrate artifact, Apr. 16, 2004, p. 1, 3 (Year: 2004).*
HPLC Expert, HPLC Hints and tips for chromatographers, Sep. 6, 2014, p. 1-2 (Year: 2014).*
Plazmasindan et al, Development and Validation of HPLC-UV Method for the Determination of Diclofenac in Human Plasma with Application to a Pharmacokinetic Study, Apr. 28, 2016, p. 1-7 (Year: 2016).*
Hecq et al., Doxorubicin-loaded drug-eluting beads (DC BEAD®) for use in transacterial chemoembolization: A stability assessment. J.Oncol. Pharm. Practice, 19(1):65-74, 2012.
Jo and Ban, Aptamer-nanoparticle complexes as powerful diagnostic and therapeutic tools, Exp. Mol. Med. 48:e230, 9 pages, 2016.
Macfarlane et al., Nanoparticle Superlattice Engineering with DNA, Science. 334:204-8, 2011.

* cited by examiner

*Primary Examiner* — Bobby Ramdhanie
*Assistant Examiner* — Donovan Bui-Huynh
(74) *Attorney, Agent, or Firm* — Haley Guiliano LLP

(57) ABSTRACT

Doxorubicin is extracted from blood using anionic material, such as a resin comprising sulfonated polystyrene divinylbenzene beads, and polyethersulfone membrane, or both. After exposing the resin and/or membrane to blood in order to remove doxorubicin therefrom, the doxorubicin maybe extracted from the resin and/or membrane by exposing the material to an extraction solution, sonicating the extraction solution to enhance release of the doxorubicin, and repeating the exposure and sonication in order to remove substantially all of doxorubicin from the resin.

6 Claims, No Drawings

METHODS AND APPARATUS FOR EXTRACTING DOXORUBICIN FROM BLOOD AND MEASURING DOXORUBICIN IN BLOOD

CROSS-REFERRENCE TO RELATED APPLICATIONS

The present application claims the benefit of provisional application 62/343,680, filed on May 31, 2016, the full disclosure of which is incorporated herein by reference.

BACKGROUND OF THE INVENTION

1. Field of the Invention

Doxorubicin is an antineoplastic (cytotoxic) chemotherapy drug, approved for the treatment of numerous types of cancer. Because of the toxicity of doxorubicin, particular care must be taken in the administration of the drug. Possible serious long term side effects of Doxorubicin include bone marrow suppression, gastrointestinal damage, and decrease in the heart's pumping capability. Therefore, there is a lifetime maximum dosage of doxorubicin a patient can receive. Each dosage is recorded in a patient's medical records, and the cumulative total dosage is tracked, so that the maximum lifetime dosage is not exceeded.

In the case of liver cancer, doxorubicin or other chemotherapeutic agent may be administered to a patient via the hepatic artery that supplies blood to the liver tumor. This procedure is referred to as transarterial chemoembolization, or TACE. Because some of the therapeutic agent delivered in this manner circulates beyond the target tissue and remains in the circulatory system, thereby exposing healthy tissue to the toxin, devices and methods have been developed to filter or otherwise remove the chemotherapeutic agent from the vessels after the agent has been delivered to the target tumor site. A filter device positioned downstream from the liver tumor is an example of such a therapy, designed to remove doxorubicin from the patient's bloodstream after it has passed through the liver tumor, in order to reduce systemic venous circulation of the drug.

Devices and methods for removing doxorubicin from the blood of a patient in order to limit the exposure of the patient to the drug have been disclosed. A catheter which can carry a resin for the in vivo extraction of doxorubicin is described in WO 2014/100201, the full disclosure of which is incorporated herein by reference. However, there remains a need in the art to quantify the amount of drug removed from the bloodstream of the patient by such devices and methods. Further, there remains a need in the art to evaluate and track the effective drug exposure of a patient, in order to monitor the lifetime dosage of the patient. Methods for extracting doxorubicin from blood have been disclosed and are described below. In addition, methods for extracting doxorubicin from filtering materials have been disclosed and are also described below.

Exemplary prior methods previously used for extracting doxorubicin (DOX) from polyvinyl alcohol resin beads comprise:

Making an Extraction Solution:
a. Mix 1 liter of 20% weight by volume KCl aqueous solution with 1 liter of absolute ethanol;
b. Shake extraction solution to ensure thorough mixing of the two liquid phases.
c. Let the excess KCl salt precipitate out of solution;
d. Filter supernatant from mixture using a solvent filter to produce the extraction solution;

Extracting DOX from a doxorubicin-loaded polyvinyl alcohol resin bead slurry:
e. Mix 3-4 ml of a premade the doxorubicin loaded polyvinyl alcohol resin bead slurry in a conical flask with 500 ml±1 ml of the filtered extraction solution;
f. Extraction of the doxorubicin from resin was performed by magnetically stirring the solution for 7 hours;

Analyzing doxorubicin eluted from the beads:
g. After 7 hours an aliquot from the extraction solution was taken and diluted 1:1 ratio with physiological water in a volumetric flask;
h. Next the sample was analyzed using an HPLC equipped with a Diode Array Detector (DAD) with excitation wavelength set at 484.

While generally effective, these methods are lengthy and not always able to achieve complete or near complete extraction, typically being able to extract no more than 90% of the doxorubicin initially loaded onto the resin. Thus, it would be desirable to provide improved methods, materials and apparatus for extracting doxorubicin from blood. It would be further desirable if such methods, materials and apparatus were suitable for both in vitro and in vivo use. At least some of these objectives will be met by the inventions described hereinafter.

Exemplary prior methods for analyzing the amount of doxorubicin in blood, as described in Reddy et al. (2005) Acta. Pharm. 55:581-91 comprises:

Mix 400 µl of blood with 100 µl of AgNO3 (30% volume solution in water)
Mix vigorously for 1 minute
Add 5 ml of methanol
Mix vigorously for 1 minute
Leave for 10 seconds
Remove the solid particulates via centrifugation
Remove the methanol via evaporation
Re-suspend in a smaller quantity of methanol
Analyze via chromatography While generally effective, this method requires multiple steps and results in two chromatographic peaks that must be added together in order to evaluate the drug concentration in blood accurately. It would be desirable to provide methods with fewer steps, which result in only a single chromatographic peak, and which display equivalent or improved accuracy in comparison with this prior method. At least some of these objectives will be met by the inventions described hereinafter.

2. Description of the Background Art

Methods and materials for extracting doxorubicin from blood are described in Reddy et al. (2005) Acta. Pharm. 55:581-91 and Hecq et al. (2012) J. Oncol. Pharm. Practice 19:65-74. A catheter which can carry a resin for the in vivo extraction of doxorubicin is described in WO 2014/100201, the full disclosure of which is incorporated herein by reference.

SUMMARY OF THE INVENTION

The present invention provides methods, materials, apparatus, and systems for extracting doxorubicin from a patient's blood, extracting doxorubicin from filter materials, performing an assay to evaluate the amount of doxorubicin removed from the blood, and tracking the effective exposure of the patient to doxorubicin in order to monitor the patient's lifetime dosage limit. The extraction may be done in vitro from blood withdrawn from the patient, where the blood is thereafter exposed to extraction materials such as ion exchange and other materials, or particular anionic resins of the present invention in an external containment vessel. More usually, however, the extraction will be done in vivo using an intravascular catheter or probe which may be placed in circulating blood of the patient so that it is exposed to the blood to remove the doxorubicin. Alternatively, the exposure could occur in an extracorporeal blood circulation circuit where the blood would be passed through a column or other conventional blood filtering assembly holding the extraction resins, as described in more detail below.

For both in vivo and in vitro protocols, the doxorubicin may be extracted from the patient's blood by exposing the blood to an anoionic material, such as a resin, membrane, a filter or other structure comprising ion exchange materials. As an example of ion exchange materials, a membrane may comprise an anionic extraction material selected from the group consisting of polystyrene divinylbenzene beads, a polyether sulfone sulfonate membrane, and a nucleic acid-derivatized filter material. Suitable DNA- and RNA-derivatized resins are described in R. J. Macfarlane et al., Nanoparticle Superlattice Engineering with DNA, *Science*. 334, 204-8 (2011), and H. Jo, and C. Ban, Aptamer-nanoparticle Complexes as Powerful Diagnostic and Therapeutic Tools, *Exp. Mol. Med.* 48, e230 (2016).

The blood will be exposed to the anionic material, e.g. a resin, typically in the form of beads of the type used in ion exchange, a membrane, or a filter substrate, for time sufficient to extract at least a portion of the doxorubicin present in the blood, often for a time sufficient to remove substantially all of the doxorubicin present in the blood. The extraction time necessary may be in a range from 30 minutes to 3 hours, typically from 60 minutes to 2 hours.

After the resin has been exposed to the blood for the desired time, the resin will be separated from the blood and exposed to an extraction solution in the presence of a detergent or a surfactant. In order to promote the release of doxorubicin, the resin beads will typically be immersed or otherwise suspended in the extraction solution which will usually be sonicated for a time in the range from 30 minutes to 120 minutes. The beads are then separated from the extraction solution resulting in a first supernatant. The separated beads are then re-suspended in fresh extraction solution, which is usually also sonicated, to remove residual doxorubicin in the beads to form a second supernatant, typically removing all of the residual doxorubicin so that the total amount of doxorubicin initially present in the beads will be present in the first and second supernatants.

In exemplary embodiments, the resin mixture comprises from 90% to 100% by weight sulfonated polystyrene divinylbenzene beads. Alternatively, a polyethersulfone membrane may be used. As yet another alternative, sulfonated polystyrene beads may be used in combination with a polyethersulfone membrane. In further exemplary embodiments, the extraction solution comprises an aqueous potassium chloride (KCl) solution combined with an organic phase, typically acetone, ethanol, or acetonitrile. Extraction solution may comprise from 1:1.5 to 1.5:1 parts aqueous KCl solution to organic phase by volume. The surfactant or detergent will typically be lipophilic and present at from about 0.5% to 2% by volume, and the surfactant maybe selected from a group consisting of CHAPS, sodium dodecyl sulfate (SDS), Triton X®-100, and CTAB.

In still further exemplary embodiments, sonicating may comprise placing the extraction solution with the resin and the surfactant in an ultrasonic bath. Alternatively, sonicating may comprise immersing a sonication probe into the extraction solution. Typically, sonication would be performed at 20 kHz to 50 kHz with the power in the range from 80 W to 400 W, and performed, for example, with a Branson Sonifier 450" sonic probe. The sonicating step maybe from a period in the range from about 15 minutes to about 1 hour. The methods of the present invention typically result in the removing from about 80% to 95% of the doxorubicin in the first extraction step and the remaining 5% to 20% of the doxorubicin in the second sonication step, with a total removal typically of at least 99% and typically in the range from 99% to 100% of the amount of doxorubicin initially present.

In a further aspect of the present invention, a resin for use in extracting doxorubicin from blood comprises a mixture of sulfonated polystyrene divinylbenzene and polyethersulfone sulfonate. The sulfonated polystyrene beads are typically present from 90% to 100% by weight. A polyethersulfone membrane may be used alternatively or in combination with the sulfonated polystyrene beads. Typically, the beads will not be loaded with doxorubicin or any other material prior to use. In other instances, however, it may be desirable to provide the beads of the present invention which are pre-loaded with doxorubicin for use in analytical and other methods.

In a still further aspect of the present invention, a catheter or probe for extracting doxorubicin from blood circulating in a patient may comprise an elongate body having a proximal end and a distal end. Usually, at least the distal end is configured to be introduced into a blood vessel lumen of the patient. The elongate body will have a chamber, usually within the distal end of the elongate body where the chamber is configured to allow blood to flow through when the catheter is present in the blood vessel lumen. The chamber will carry the resin of the present invention as described above. Exemplary catheters useful in the present invention are described in WO2014/100201, the full disclosure of which is incorporated herein by reference. The catheters may be positioned in different blood vessels including the hepatic vein, iliac vein, inferior vena cava, renal vein, and superior vena cava. Additional exemplary locations include, intracranial in the dural venous sinuses (e.g., sigmoid sinus, transverse sinus, torcula, straight sinus, superior sagittal sinus) to remove doxorubicin during cerebral embolization or chemoinfusion; internal jugular vein with the device inserted, for example, either transfemorally or directly in the ipsilateral internal jugular vein, for head and neck tumors and during cerebral embolization or chemoinfusions; and the brachiocephalic vein between the superior vena cava and the internal jugular vein.

The methods of the present invention may be characterized by the following features and advantages:
 a. Use of an ion exchange material comprising a mixture of sulfonated polystyrene divinylbenzene copolymer and polyether sulfone sulfonate.
 b. Use of multiple extraction solutions comprising 65%-45% organic solution, 65%-45% aqueous KCl (20% w/v), and 1% weight by volume of a lipophilic surfactant (which adds to the displacement of doxorubicin from ion exchange material).
 c. Facilitating mixing by ultrasonication produced by a probe or in an ultrasonic bath. Particular ultrasonic frequencies are used to create mechanical pressure waves and imploding cavitation bubbles to agitate the beads in extraction solution.

d. Ultrasonication also produces heat in the extraction solution (by molecular friction) which further enhances the extraction of doxorubicin from the ion exchange material.
e. Replacing the extraction solution half way through the method facilitates extracting the remaining 10%-15% of drug bound to the beads.
f. Extraction efficiency is 99%-100% of drug bound to ion exchange material.
g. Peak doxorubicin elution concentration may be reached at one hour.

The present invention further provides methods for measuring doxorubicin in a patient's blood. A sample of the patient's blood, typically from 75 μl to 125 μl, is vigorously mixed with a from 15 μl to 35 μl of a silver nitrate solution, typically 25% to 35% by weight, wherein the total mixed volume is below 200 μl. A volume less than or equal to 1 ml of methanol is added to the mixture, typically from 750 μl to 1 ml, and the resulting combination further mixed for at least 10 minutes. The mixed blood, silver nitrate, and methanol are then let stand for at least 30 minutes, typically for 60 minutes, to precipitate particles, and the particles analyzed via chromatography as described in greater detail below.

The drug detection method involves the use of a high pressure liquid chromatography column (HPLC) to measure the concentrations of drug by absorbance and fluorescent spectroscopy. The C18 column used is a Waters Spherisorb ODS 2 Column, 5 μm, 4.6×250 mm, and chromatographic separation was performed at a flow rate of 1 ml/min. The method utilizes an isocratic gradient of 50% Acetonitrile and 50% $NaH_2PO_4$ buffer solution. Fluorescence excitation/emission wavelengths used to measure Doxorubicin concentration are 480 nm/560 nm respectively. UV absorbance is measured at 254 nm and 480 nm. Samples were run between 10-60 minutes, and the retention times of drug occur around 7-20 minutes.

These methods provide a number of advantages relative to prior methods for doxorubicin measurement in blood, including requiring fewer, using smaller sample and reagent sizes, and generating a single chromatographic peak that provides more accurate results.

DETAILED DESCRIPTION OF THE INVENTION

Extraction solutions suitable for use in the present invention may be prepared as follows:
a. Solution 1
  i. Mixing 100 ml of 20% weight by volume KCl solution with 100 ml of organic solution (acetone, ethanol, or acetonitrile)
  ii. After excess salt has precipitated, take off the extraction solution supernatant and add 1% weight by volume of detergent (CHAPS, SDS, Triton X-100, or CTAB).
  iii. After 1 hour of stirring, spin down the detergent extraction solutions, to remove excess precipitates, then filter supernatant using a solvent filter.
b. Solution 2
  i. Mixing 120 ml of 20% weight by volume KCl solution with 80 ml of organic solution (acetone, ethanol, or acetonitrile) making the ending concentration 60% KCL and 40% organic.
  ii. After excess salt has precipitated take off the extraction solution supernatant add 1% weight by volume of detergent (CHAPS, SDS, Triton X-100, or CTAB).
  iii. After 1 hour of stirring spin down the detergent extraction solutions, to remove excess precipitates, then filter supernatant using a solvent filter.
c. Solution 3
  i. Mixing 80 ml ml of 20% weight by volume KCL solution with 120 ml of organic solution (acetone, ethanol, or acetonitrile) making the ending concentration 40% KCL and 60% organic.
  ii. After excess salt has precipitated take off the extraction solution supernatant add 1% weight by volume of detergent (CHAPS, SDS, Triton X-100, or CTAB).
  iii. After 1 hour of stirring spin down the detergent extraction solutions, to remove excess precipitates, then filter supernatant using a solvent filter.
d. Solution 4
  i. Mixing 90 ml of 20% weight by volume KCL solution with 110 ml of organic solution (acetone, ethanol, or acetonitrile) making the ending concentration 45% KCL and 55% organic.
  ii. After excess salt has precipitated take off the extraction solution supernatant add 1% weight by volume of detergent (CHAPS, SDS, Triton X-100, or CTAB).
  iii. After 1 hour of stirring spin down the detergent extraction solutions, to remove excess precipitates, then filter supernatant using a solvent filter.

Doxorubicin may be removed from blood in vivo or in vitro by exposure of the blood to an ion exchange resin. For example, doxorubicin may be removed from blood by exposure to cationic resin comprising a mixture of sulfonated polystyrene divinylbenzene beads and/or polyethersulfone sulfonate membrane.

In vivo removal of doxorubicin from a patient may be accomplished by incorporating the cationic sulfonated polystyrene divinylbenzene resin or beads, and/or polyethersulfone sulfonate membrane into the filtration catheters described in PCT Publication WO 2014/100201, previously incorporated herein by reference. The filtration device may then be positioned with a patient's blood vessel, as described in the PCT Publication and left in place for a time sufficient to remove doxorubicin until the resin is partially or fully loaded and/or the doxorubicin is partially or completely removed from the blood.

Once the cationic sulfonated polystyrene divinylbenzene and polyethersulfone sulfonate resin bead mixture of the present invention is partially or fully loaded with doxorubicin, the doxorubicin may be extracted from a portion of the bead mixture as follows:
a. Add 0.19 grams of loaded resin/membrane to a 50 ml falcon tube.
b. Then add 50 ml of extraction solution to the container.
c. To extract doxorubicin from the ion exchange material we place the extraction solution with the loaded beads under ultrasonic mixing by using an ultrasonic bath or an ultrasonic probe for 30 minutes.
d. After 30 minutes take a 1 ml sample/aliquot from the bead containing extraction solution.
e. Then decant the drug filled supernatant after the beads are allowed to settle out of solution.
f. Add 50 ml of extra extraction solution to the container holding the beads.

g. Now ultrasonically mix the new bead containing extraction solution using an ultrasonic bath or an ultrasonic probe for 30 minutes to extract.

Doxorubicin extracted from the beads may be analyzed as follows:
  a. After 1 hour under ultrasonic mixing/reloading of the extraction solution all of the doxorubicin has eluted off of the ion exchange material.
  b. Samples analyzed using a Molecular Devices Spectramax M2 Multi-Mode or, in the alternative, high pressure liquid chromatography (HPLC) absorbance and fluorescence microplate reader measuring excitation at 480 nm and emission at 550 nm.
  c. Doxorubicin concentrations are compared to standard concentration curves.

Doxorubicin in blood may be analyzed by performing the following steps:
  Mix 100 µl of blood with 25 µl of AgNO3 (30% volume solution in water)
  Mix vigorously for 15 seconds
  Add 875 µl of Methanol
  Mix vigorously for 15 minutes
  Leave for 60 minutes
  Remove the solid particulates via centrifugation
  Analyze via chromatography This method requires fewer steps than the prior method described earlier, uses smaller sample and reagent sizes, and results in a single peak that provides more accurate results.

One or more business methods may incorporate the methods described above. As an example of a business method, hospital or clinic customers may perform extractions for a patient, and then send the device (such as a catheter) used in the extraction to a service provider. The service provider may then perform an analysis of the device, and/or of the filtration materials as described above, in order to quantify the amount of therapeutic removed from the blood of the patient.

Following analysis via chromatography in one of the methods described above, the amount of doxorubicin extracted from a patient's circulatory system is determined. The amount of doxorubicin extracted may be entered into a formula in order to determine the effective dosage to the patient. And the effective dosage to the patient may be recorded in order to track a patient's cumulative lifetime dosage.

For example, prior to a patient's first treatment, the prescribed dosage ($Dosage^{PRE}$) is recorded, and the drug administered to the patient. A filtering device is employed as described above in order to remove chemotherapeutic agent from the bloodstream after it has passed through the target tissue. The amount of agent extracted from the filter material is calculated according to the methods described above, and quantified as the extracted dosage ($Dosage^{EXT}$). The extracted dosage is subtracted from the prescribed dosage, in order to determine a first effective dosage to the patient ($Dosage^{EFF}$ 1):

$$Dosage^{PRE} - Dosage^{EXT} = Dosage^{EFF} 1$$

The first effective dosage is recorded and maintained in the patient's medical chart. In subsequent treatments, the effective dosage is analyzed and recorded, and assigned a subsequent number. Each successively numbered effective dosage is added to the previous effective dosage, thereby tracking the total lifetime dosage ($Dosage^{LIFE}$).

$$Dosage^{EFF} 1 + Dosage^{EFF} 2 + Dosage^{EFF} 3 = Dosage^{LIFE}$$

A kit comprising individually packaged devices and reagents as described above may be assembled and sold commercially. A kit, for example, may include:
  1: Catheter having a reservoir containing sulfonated polystyrene beads;
  2: 3 vials KCl solution: 100 ml; 120 ml; 90 ml
  3: 3 vials of Ethanol solution: 100 ml; 80 ml; 110 ml
  4: Detergent
  5: Instructions for use: catheter, extraction methods and formula The foregoing examples are not intended to limit the scope of the invention. All modifications, equivalents and alternatives are within the scope of the invention. As an example, therapeutic agents other than Doxorubicin may be filtered from a patient's blood, the filtered agent extracted and quantified, and the lifetime dosage of the agent tracked.

What is claimed is:

1. A method for measuring doxorubicin present in a patient's blood, said method comprising:
  mixing a sample of the patient's blood with a silver nitrate solution;
  adding a volume of methanol to the mixture;
  further mixing the blood, silver nitrate, and methanol together for at least 10 seconds;
  letting the mixed blood, silver nitrate, and methanol stand for at least 30 minutes to precipitate particles and form a supernatant;
  separating the supernatant via chromatography, wherein the separated supernatant contains doxorubicin originally present in the blood sample; and
  analyzing the separated supernatant via spectroscopy, wherein the UV absorbance of doxorubicin is measured.

2. The method of claim 1, including the step of analyzing the separated supernatant via spectroscopy at 254 nm.

3. The method of claim 1, including the step of analyzing the separated supernatant via spectroscopy at 480 nm.

4. The method of claim 1, wherein a chromatography buffer comprises acetonitrile and $NaH_2PO_4$.

5. The method of claim 1, wherein the total mixed volume of the sample of the patient's blood with the silver nitrate solution is below 200 µl.

6. The method of claim 1, wherein the volume of methanol added to the mixture is less than or equal to 1 ml.

* * * * *